United States Patent [19]

Yousefian

[11] Patent Number: 5,536,169

[45] Date of Patent: Jul. 16, 1996

[54] FULL ARCH SPRING ORTHODONTIC RETAINER

[75] Inventor: Joseph Z. Yousefian, Bellevue, Wash.

[73] Assignee: Pro-Orthoappliance Corporation, Bellevue, Wash.

[21] Appl. No.: 511,979

[22] Filed: Aug. 7, 1995

[51] Int. Cl.$^6$ .............................................. A61C 3/00
[52] U.S. Cl. .............................................................. 433/6
[58] Field of Search ...................... 433/6, 7, 171, 433/199.1

[56] References Cited

U.S. PATENT DOCUMENTS

| | | |
|---|---|---|
| 4,055,895 | 11/1977 | Huge . |
| 4,253,828 | 3/1981 | Coles et al. ................................ 433/6 |
| 4,370,129 | 1/1983 | Huge . |
| 4,413,978 | 11/1983 | Kurz ........................................ 433/6 |
| 4,448,735 | 5/1984 | Huge . |
| 4,676,745 | 6/1987 | Zurita ....................................... 433/6 |
| 4,752,222 | 6/1988 | Bass . |
| 4,793,803 | 12/1988 | Martz . |
| 4,913,654 | 4/1990 | Morgan et al. . |
| 4,976,614 | 12/1990 | Tepper . |
| 5,022,855 | 6/1991 | Jeckel . |
| 5,067,896 | 11/1991 | Korn . |
| 5,096,416 | 3/1992 | Hulsink . |
| 5,145,364 | 9/1992 | Martz et al. . |
| 5,415,542 | 5/1995 | Kesling . |

FOREIGN PATENT DOCUMENTS

| | | | |
|---|---|---|---|
| 2461180 | 7/1975 | Germany ................................. | 433/6 |

OTHER PUBLICATIONS

Professional Positioners, Inc. brochure, *Pro Orthodontic Laboratory–Orthodontic Laboratory Services*, 3 pp., date uncertain.

*Primary Examiner*—Cary E. O'Connor
*Attorney, Agent, or Firm*—Christensen, O'Connor, Johnson & Kindness

[57] ABSTRACT

An orthodontic appliance (10) fits to the teeth (16) of a patient (14) and substantially retains the teeth in a desired arrangement. The appliance includes a plurality of arcuate polymer strips (20). The strips substantially corresponding in shape to different sections of the lingual arch-shapes defined by the lateral surfaces of the teeth. At least one of the polymer strips is a lingual strip (20d), and at least one of the other polymer strips is a labial strip (20a), (20b), or (20c). Additionally, the appliance includes a wire (22) extending through the lengths of the strips, which connects the strips to one another in a spaced-apart relationship. The wire includes transverse adjusting segments (32) for adjusting the fit of the orthodontic appliance. Each transverse adjusting segment extends from between a pair of the strips in a direction generally transverse to the lengths of the strips.

22 Claims, 4 Drawing Sheets

FULL ARCH SPRING ORTHODONTIC RETAINER

FIELD OF THE INVENTION

The present invention relates generally to orthodontic appliances, and more particularly to orthodontic appliances known as retainers.

BACKGROUND OF THE INVENTION

Conventional active orthodontic appliances apply forces to the teeth of a patient. The forces gradually move the teeth into an arrangement that is more cosmetically appealing and/or functional. That is, the arrangement provides the patient with an improved appearance, and/or improved ability to chew, speak, and/or perform other functions.

Unfortunately, for a period of time after a patient ceases wearing an active orthodontic appliance, the teeth usually will shift from the desired arrangement. Therefore, generally patients wear a passive orthodontic retainer, for a period of time after the teeth have been moved into the desired arrangement by one or more active appliances. Patients wear the retainers to prevent their teeth from shifting until the teeth have stabilized in the desired arrangement.

However, conventional retainers have several problems. First, retainers are visible to others while the patient is wearing the retainer. Thus, patients consider retainers to be cosmetically undesirable. This is particularly true for retainers which must be worn 24 hours a day to prevent tooth movement. One attempted solution to this problem has been to make retainers removable. The patient removes such a retainer during the waking hours, and inserts the retainer only for sleeping. Notwithstanding, frequently the patient's teeth will shift in just a few hours, making insertion of the retainer for sleeping difficult.

Second, a retainer can cause difficulty in chewing. While retainers are generally less intrusive than an active orthodontic appliance, nonetheless such retainers often impair the patient's ability to chew and/or speak. This is especially true of retainers that include wires or ligatures that extend over the occlusal surfaces of the patient's teeth, and/or other structures that extend into the palette area of the patient's mouth.

Third, retainers generally only provide retention forces, which makes them passive orthodontic appliances. Thus, retainers cannot shift the teeth to a more desired arrangement. Notwithstanding, occasionally a situation requires the repositioning of one or two malposed teeth, which can only be accomplished by a more intrusive active appliance. To minimize the impact on the patient, a retainer is desired, rather than a conventional active appliance, that can reposition the malposed teeth, while maintaining the position of the other teeth.

The present invention provides an improved solution to these problems.

SUMMARY OF THE INVENTION

The present invention provides an orthodontic appliance for use as a retainer. An appliance in accordance with the present invention may be fitted to either the upper or lower teeth of the patient. When properly used, the appliance retains the teeth to which it is fitted in a desired arrangement. The appliance need only be worn at night while the patient is sleeping. The appliance is resilient and can fit around teeth that may have shifted slightly during the waking hours while the appliance was not being worn. When reapplied at night, the resilient nature of the appliance allows it to fit around the shifted teeth, and additionally shifts the teeth back to the desired arrangement. The appliance may also be used to move a single malposed tooth a limited distance.

The appliance includes a plurality of arcuate polymer strips. The strips substantially correspond in shape to different sections of the lingual arch-shapes defined by the lateral surfaces of the teeth. At least one of the polymer strips is a lingual strip, corresponding in shape to a section of the inner lingual arch-shape defined by the lateral surfaces of the teeth. At least one of the other polymer strips is a labial strip, which is used herein to refer to a strip which substantially corresponds in shape to a section of either the outer labial or buccal arch-shape defined by the lateral surfaces of the teeth.

Additionally, the appliance includes a wire extending through the lengths of the polymer strips, which connects the polymer strips to one another in a spaced apart relationship. The wire includes a lingual section extending through at least one lingual strip, a labial section extending through at least one labial strip, and a distal segment connecting the lingual and labial sections of the wire to one another.

The wire preferably includes transverse adjusting segments for adjusting the fit of the orthodontic appliance. Each transverse adjusting segment extends arcuately from between a pair of polymer strips in a direction generally transverse to the lengths of the pair of polymer. Preferably, the transverse adjusting segments extend from between pairs of lingual strips. In alternate embodiments, the transverse adjusting segments may extend from between pairs of labial strips, or between pairs of lingual and labial strips, as well.

In another alternate embodiment, the distal segment of the wire may be formed into a loop. When the distal segment of the wire forms a loop, the appliance may be adjusted to apply force along the lingual arch-shape defined by the teeth. This also causes the appliance to apply force transversely to the lingual arch-shape of the teeth for moving a malposed tooth to a desired position.

In embodiments of appliances in accordance with the present invention, the appliances fit around the lateral surfaces of the teeth. Thus, the appliances permit full, and uninterrupted occlusion and interdigitation of the teeth. More particularly, the appliances do not have structure extending across the occlusal surfaces of the teeth, or into the upper palette region of the patient's mouth. Hence, the appliances are minimally intrusive, and substantially do not interfere with chewing or speaking.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENTS

Figure 1:
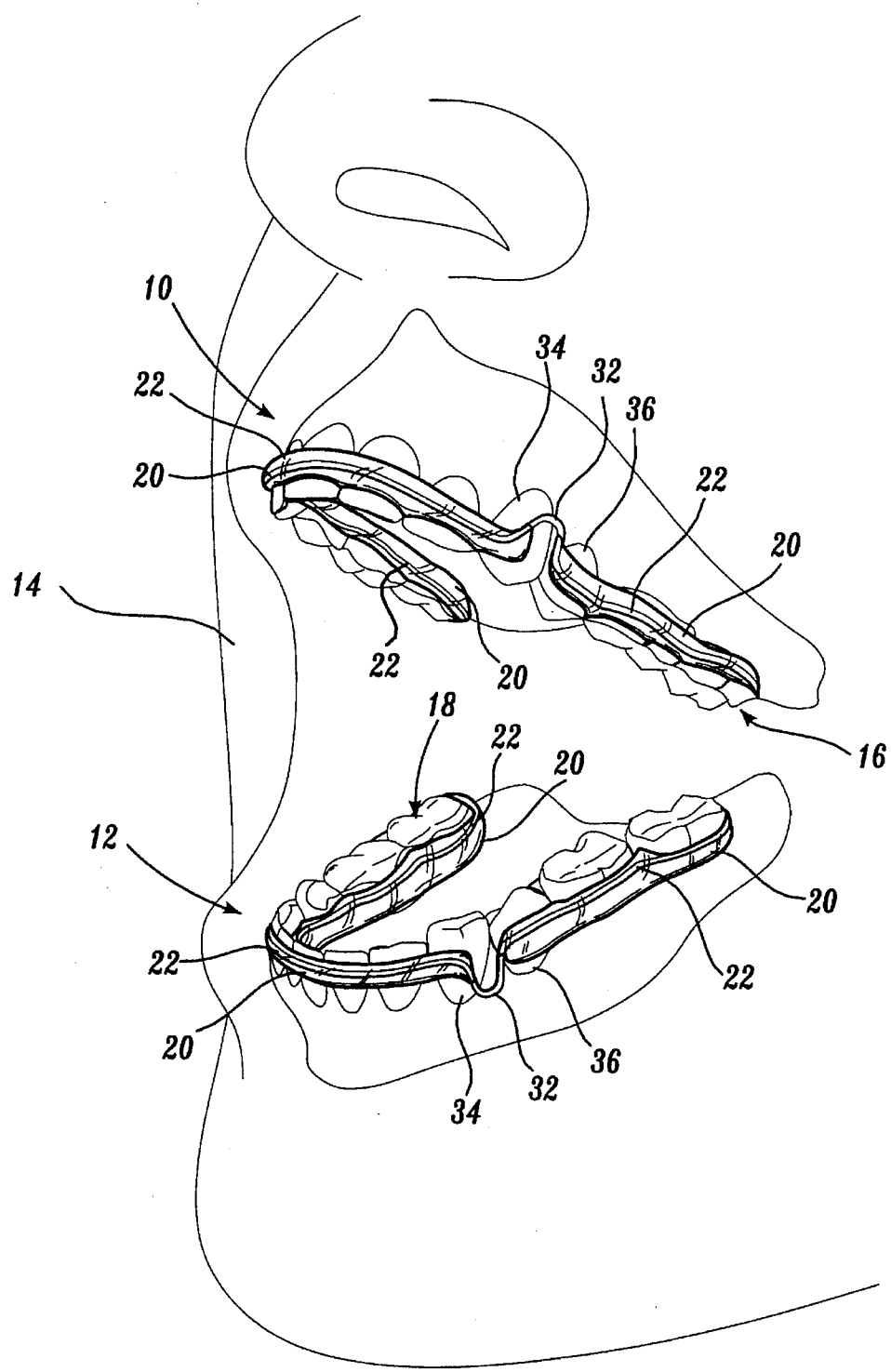
FIG. 1 illustrates a perspective view of a preferred embodiment of upper and lower orthodontic appliances in accordance with the present invention being worn on the teeth of a patient.

FIG. 1 illustrates a preferred embodiment of an upper orthodontic appliance 10 and a lower orthodontic appliance 12, both of which are in accordance with the present invention. FIG. 1 illustrates a patient 14 wearing the upper appliance 10 on his upper teeth 16, and wearing the lower appliance 12 on his lower teeth 18. The appliances 10 and 12 are substantially identical to one another, with the exception that the upper appliance is adapted to fit closely to the upper teeth 16, and the lower appliance is adapted to fit closely to the lower teeth 18.

In this regard, the appliances 10 and 12 each include a plurality of polymer strips 20. The strips 20 each extend longitudinally along a different section of the lingual arch-shape defined by the teeth 16 and 18 that the appliance is adapted for fitting. The strips 20 of the upper appliance 10 extend along different sections of the lingual arch-shape defined by the upper teeth 16, while the strips 20 of the lower appliance 12 extend along different sections of the lingual arch-shape defined by the lower teeth 18. The strips 20 extend along both the inner, or lingual surfaces, and the outer, or labial and buccal, surfaces of the teeth 16 and 18. The strips 20 each substantially correspond in shape to the section of the lingual arch-shape that a particular strip lies along.

Figure 3:
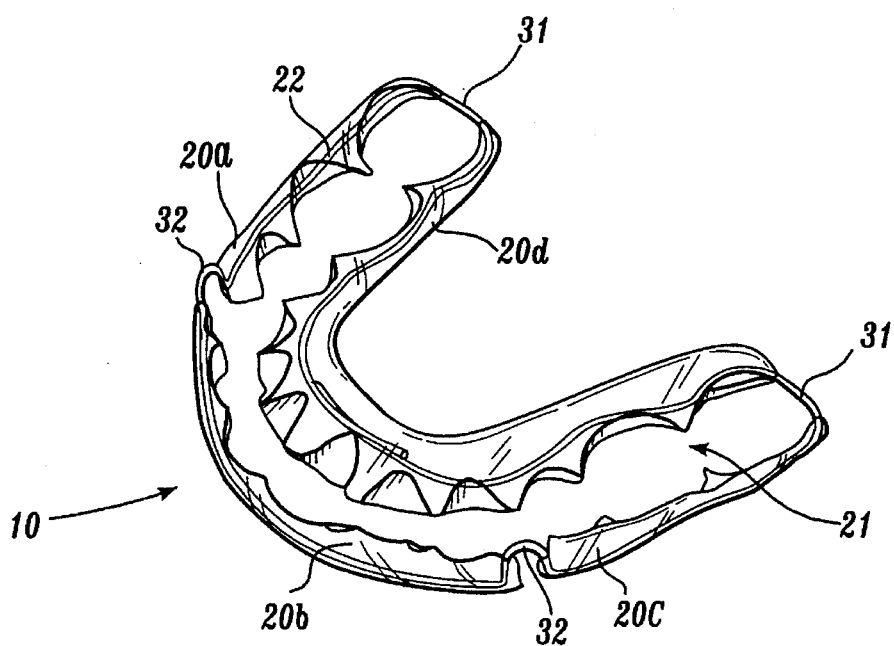
FIG. 3 illustrates a perspective view of the upper orthodontic appliance of FIG. 1 removed from the patient's teeth.

To form the strips 20, a plaster cast of the teeth 16 and 18 of the patient 14 is first made. Thereafter, strips of a polymer material are laid along the cast of the teeth 16 and 18 to form strips 20 substantially corresponding in shape to sections of the lingual arch-shape defined by the teeth. Referring to FIG. 3, this results in strips 20 having lateral projections 21 defined in the sides of the strips that correspond to and fill the undercut areas of the lateral surfaces of the adjacent teeth 16 and 18 and the spaces between the teeth. The projections 21 closely correspond in shape to the lateral surfaces of the teeth 16 and 18 so that the strips 20 fit closely against, and engage the teeth for exerting forces thereagainst.

For cosmetic purposes, a clear polymer is used to form the strips 20. A suitable polymer for forming the strips is a castable acrylic. Forming the strips 20 of a clear polymer minimizes the visibility of the appliances 10 and 12 when worn by the patient 14. The polymer may be a self-curing type, but is preferably cured under heat and controlled pressure conditions to remove bubbles for increased transparency of the strips 20.

A wire 22 extends through the length of each of the strips 20. For corrosion resistance, stainless steel forms the wire. Preferably, the wire has a diameter of approximately 0.03 inches.

The wire 22 is embedded in the strips 20 prior to curing the polymer material forming the strips. That is, the wire 22 is placed in the strips 20 while the polymer material is substantially fluid. When the polymer strips 20 cure, the wire 22 is held tightly in the strips.

Figure 2A:
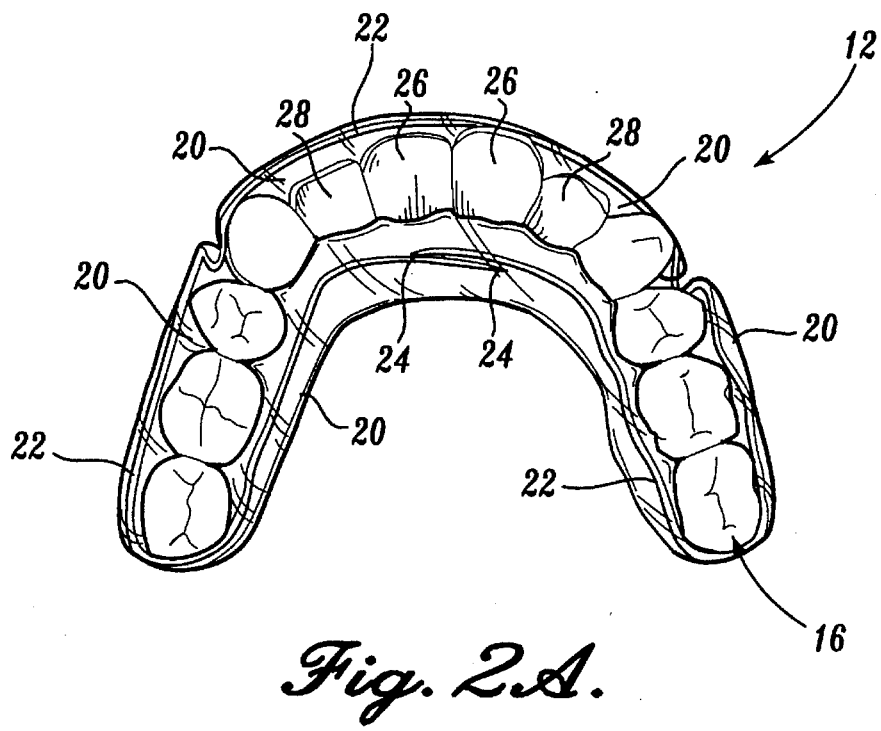
FIG. 2A illustrates a plan view of only the patient's upper teeth while wearing the upper orthodontic appliance of FIG. 1, looking towards the occlusal surfaces of the upper teeth.
Figure 2B:
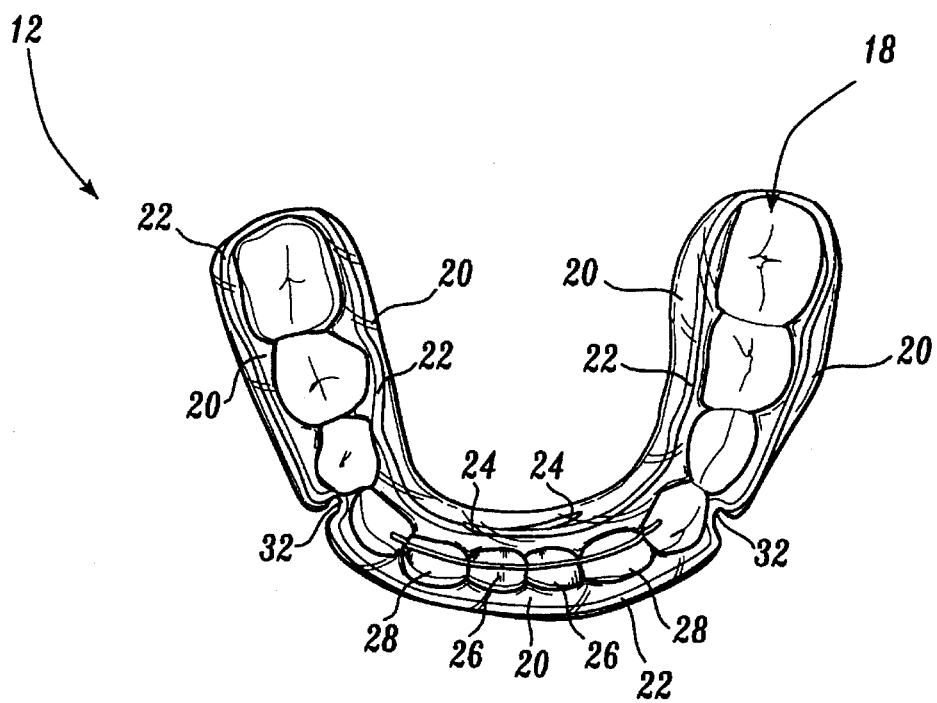
FIG. 2B illustrates a plan view of only the patient's lower teeth while wearing the lower orthodontic appliance of FIG. 1, looking towards the occlusal surfaces of the lower teeth.

The wire 22 connects the strips 20 to one another, and properly positions the strips relative to one another. Referring to FIGS. 2A and 2B, the wire 22 is bent into a loop passing around the lingual and labial surfaces of the teeth 16 and 18. Thus, the wire 22 holds the strips 20 against the lingual and labial surfaces of the teeth 16 and 18.

The ends 24 of the wire 22 overlap one another for a short distance behind the central and lateral incisors 26 and 28 of the teeth 16 and 18 to avoid fracture of the polymer. The ends 24 are located in a strip 20, which retains the ends. As shown in FIG. 2B, the lower appliance 12 can fit behind and underneath a conventional bonded retainer 30, which is adhered across the upper lingual surfaces of the central lower teeth 18.

The wire 22 spaces the ends of the strips 20 away from another. With reference to FIG. 3, the upper appliance 10 includes three labial strips 20a, 20b, and 20c for fitting against the labial and buccal surfaces of a patient's teeth. The end strips 20a and 20c are for fitting against the buccal surface of the posterior teeth. The central strip 20b extends between the end strips 20a and 20b for fitting against the labial surfaces of the central teeth. The wire 22 maintains the ends of the end strips 20a and 20c spaced from the ends of the central strip 20b.

The appliance 10 also includes a single lingual strip 20d for fitting against the lingual surfaces of the patient's teeth. Distal segments 31 of the wire 22 extend from the ends of the lingual strip 20d to the posterior-most ends of the two end labial strips 20a and 20c. The distal segments 31 are for extending behind the patient's posterior-most molars.

Additionally, the wire 22 includes adjusting segments 32 extending from between the ends of the labial strips 20a, 20b, and 20c. The adjusting segments 32 are arched-shaped sections or loops of the wire 22 extending in a direction generally transverse to the lengths of the strips 20a, 20b, and 20c. Specifically, the adjusting segments 32 extend in a direction perpendicular to the longitudinal axis of an individual tooth. When the patient 14 wears the appliance 10 as shown in FIG. 1, the adjusting segments 32 extend towards the roof of the patient's mouth. The lower appliance 12 has a similar construction, except that the adjusting segments 32 extend in the opposite direction. That is, when the patient 14 wears the lower appliance 12, the adjusting segments 32 extend towards the patient's lower jaw.

The adjusting segments 32 permit the fit of the appliances 10 and 12 to be adjusted. Since the adjusting segments 32 extend from between the polymer strips 20, i.e., the segments are not embedded in the polymer, the arch forming the segments may be bent to adjust the fit of the appliances 10 and 12. Preferably, the appliances 10 and 12 are formed so that the adjusting segments 32 lie proximate the first bicuspids 34 and canines 36.

The adjusting segments 32 of appliances 10 and 12 extend only from the labial sections of the wire 22. That is, the adjusting segments 32 extend only from the section of the wire 22 proximate the labial surfaces of the teeth 16 and 18. Generally, this is sufficient to adjust the fit of the appliances 10 and 12.

Figure 4:
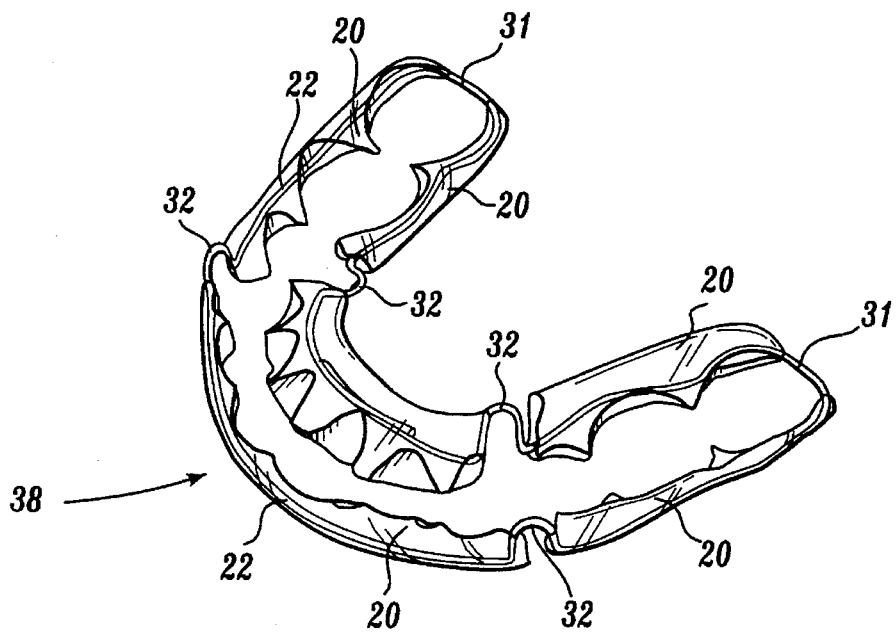
FIG. 4 illustrates a perspective view of an alternate embodiment of an upper orthodontic appliance in accordance with the present invention having opposing transverse adjusting segments.

In alternate embodiments, adjusting segments 32 may also extend from the lingual section of the wire 22, i.e., the section of wire proximate the lingual surfaces of the teeth 16 and 18. FIG. 4 illustrates an alternate embodiment of an orthodontic appliance 38 in accordance with the present invention having both labial and lingual adjusting segments 32. More particularly, the appliance 38 is substantially identical to the previously described embodiments, except that it includes adjusting segments 32 extending from both the labial and lingual sections of the wire 22. Additionally, the appliance 38 includes three lingual strips 20, rather than a single longer lingual strip as in the previous embodiments, for extension of the lingual adjusting segments 32.

The labial and lingual adjusting segments 32 generally oppose one another on opposite sides of the teeth 16 and 18 when the patient 14 wears the appliance 38. The appliance 38 is useful for exerting control over an extraction space. That is, the adjusting segments 32 can be adjusted to bear against the teeth 16 and 18 to restrain teeth from moving and opening the extraction space.

Figure 5:
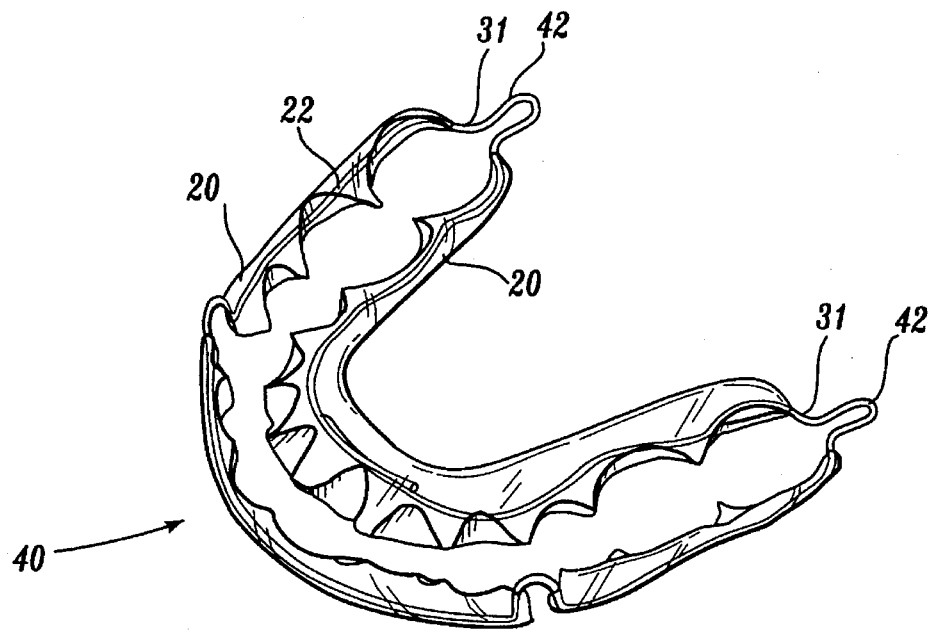
FIG. 5 illustrates a perspective view of another alternate embodiment of an upper orthodontic appliance in accordance with the present invention having distal adjusting segments.

FIG. 5 illustrates another alternate embodiment of an orthodontic appliance 40 in accordance with the present invention. The appliance 40 is substantially identical to the previously described preferred embodiments, with one primary exception. Namely, the appliance 40 includes distal adjusting segments 42.

Specifically, the sections of wire 22 extending from the lingual to the labial portions of the appliance 40 are in an arch-shape forming the distal adjusting segments 42. The arch-shape of the distal adjusting segments 42 extends rearwardly behind the patient's posterior-most molars.

The appliance 40 can be used to move a malposed tooth. More particularly, if the arch-shape forming the distal adjusting segments 42 is narrowed, the labial and lingual portions of the appliance are drawn towards one another. This causes the appliance 40 to exert a transverse force against a malposed tooth to gradually move the tooth to a desired position. As the malposed tooth moves, the distal adjusting segments 42 can be narrowed so that the appliance 40 exerts approximately the same force against the tooth until the malposed tooth is properly positioned.

Figure 6:
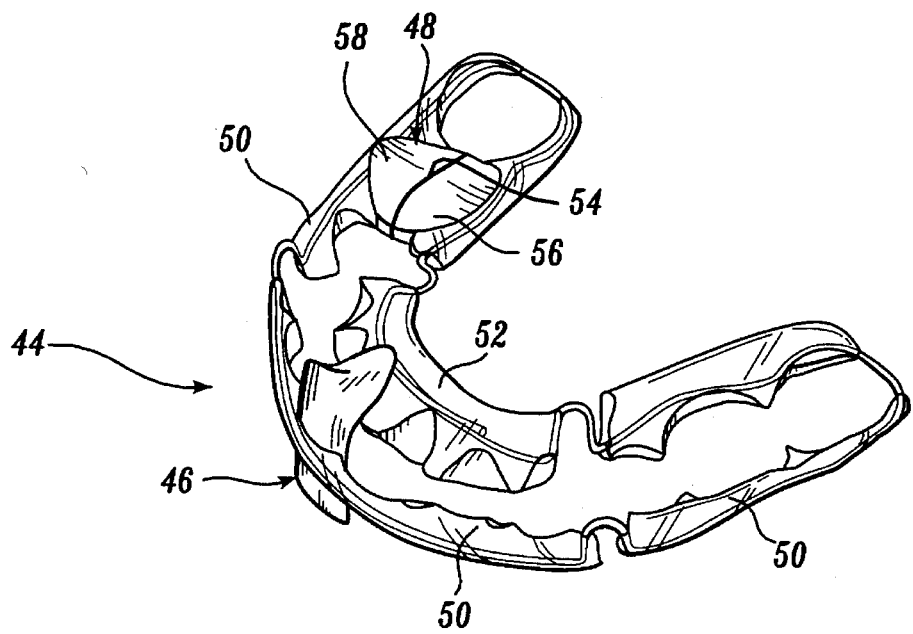
FIG. 6 illustrates a perspective view of another alternative embodiment of an upper orthodontic appliance in accordance with the present invention having artificial teeth.

FIG. 6 illustrates another alternate embodiment of an orthodontic appliance 44 in accordance with the present invention. The appliance 44 is substantially identical to the previously described preferred embodiments, except that it includes a pair of artificial teeth 46 and 48. The artificial teeth 46 and 48 cosmetically replace teeth the patient may be missing. Additionally, the artificial teeth 46 and 48 can prevent the remaining teeth from moving into the locations formerly occupied by the missing teeth.

A polymer material forms the artificial teeth 46 and 48. The artificial teeth 46 and 48 may be formed integrally with polymer material forming the strips 20, or formed separately and bonded thereto. Preferably, the polymer material forming the artificial teeth 46 and 48 is colored to approximately match the color of natural teeth, rather than being clear like the strips 20.

The anterior-most artificial tooth 46 fills the space formerly occupied by a lateral incisor when the patient wears the appliance 44. Preferably, the anterior-most artificial tooth 46 only connects to a lingual strip 50, and not to a labial strip 52. The reason for this as follows.

The wire 22 used in the appliances 10, 12, 38, 40 and 44 is resilient, and is capable of flexing for removal and replacement on a patient's teeth. Thus, the patient 14 may wear the appliances only part of the time, such as when sleeping. If the patient's teeth shift during the time the appliance is removed, the resilient nature of the wire 22 allows the appliance to still fit over the teeth. Further, the wire 22 will resiliently urge the teeth back to the desired arrangement, so that the teeth return to the desired locations.

Connecting an artificial tooth to both the lingual and labial portion of the appliance 44 decreases the amount of resilience in the appliance. Thus, the anterior-most artificial tooth 46 only connects to one portion of the appliance 44. Preferably, the anterior-most artificial tooth 46 connects to the lingual portion of the appliance to conceal the connection for cosmetic purposes.

The other artificial tooth 48 fills the space formerly occupied by a molar. The artificial tooth 48 is cut in half along line 54 to form a lingual tooth half 56 and a labial tooth half 58. The lingual half 56 connects to a lingual strip 52, while the labial half connects to a labial strip 50. Cutting the artificial tooth 48 in half 48 preserves the resilient nature of the appliance 44. Preferably, an artificial tooth for replacing a molar is preferably cut in half in this manner because the tooth is thicker, it securely attaches the tooth to the appliance 44, and the tooth is less visible than an anterior tooth.

The above-described appliances 10, 12, 38, 40 and 44 have a number of advantages. First, as previously noted, the appliances are resilient. Thus the patient can forego wearing such an appliance for significant periods of the day. If the patient's teeth shift, the appliance resiliently accommodates the shifted positions of the teeth, and urges the teeth back to the desired arrangement.

Second, the appliances do not include any structure passing over the occlusal surfaces of the teeth, such as a tooth clasp. Further, in this regard, the appliances do not include any structure extending into the palette region of the patient's mouth. Rather, the appliances fit only around the lateral surfaces of the teeth. The appliances therefore substantially do not interfere with chewing or speaking, are minimally intrusive, and permit full, uninterrupted occlusion of the upper and lower teeth.

Third, the appliances function both passively and actively. The appliances function passively as a retainer for retaining teeth in a desired arrangement. However, the appliances are also active because they resiliently urge the teeth back to the desired arrangement if the teeth shift slightly. Additionally, the distal adjusting segments 42 permit the appliances to actively reposition a malposed tooth. There are other advantages as well.

While the preferred embodiment of the invention has been illustrated and described, it will be appreciated that various changes can be made therein without departing from the spirit and scope of the invention. For example, the transverse adjusting segments 32 could extend in the opposite direction, the ends of the wire 22 could be welded together, or the wire could be formed from a continuous loop. In view of these and other alterations, substitutions and modifications that could be made by one of ordinary skill in the art, it is intended that the scope of letters patent granted hereon be limited only by the definitions of the appended claims.

The embodiments of the invention in which an exclusive property or privilege is claimed are defined as follows:

1. An orthodontic retainer for a patient, the patient having opposite sides and teeth having lateral surfaces which define an inner lingual arch extending from one side of the patient to the other, and an outer labial arch extending from one side of the patient to the other, the orthodontic retainer comprising:

(a) a plurality of arcuate polymer strips, the polymer strips substantially corresponding in shape to different sections of the patient's lingual and labial arches, at least one of the polymer strips being a lingual strip substantially corresponding in shape to a section of the patient's inner lingual arch and at least one of the polymer strips being a labial strip substantially corresponding in shape to a section of the patient's outer labial arch; and (b) a wire extending through the lengths of the polymer strips, and connecting the polymer strips to one another to retain the lingual strip spaced-apart from the labial strip to receive the patient's teeth therebetween, the wire including:

(i) a lingual section extending through the at least one lingual strip;

(ii) a labial section extending through the at least one labial strip;

(iii) a distal segment connecting the lingual and labial sections of the wire to one another; and (iv) a first transverse adjusting segment for adjusting the fit of the orthodontic appliance, the adjusting segment extending from between a pair of polymer strips in a direction generally transverse to the lengths of the pair of polymer strips.

2. The orthodontic retainer of claim 1, wherein the wire further comprises a second transverse adjusting segment spaced apart from the first transverse adjusting segment.

3. The orthodontic retainer of claim 2, further comprising a plurality of lingual strips, and a plurality of labial strips, wherein one of the transverse adjusting segments extends from between a pair of adjacent lingual strips, and the other transverse adjusting segment extends from between a pair of adjacent labial strips.

4. The orthodontic retainer of claim 1, wherein the distal segment forms a rearwardly extending arch-shape.

5. The orthodontic retainer of claim 1, further comprising an artificial tooth secured to at least one of the polymer strips.

6. The orthodontic retainer of claim 5, wherein the artificial tooth is connected to a lingual strip.

7. The orthodontic retainer of claim 5, wherein the artificial tooth is cut in half to form two halves, one half being connected to a lingual strip, and the other half being connected to a labial strip.

8. The retainer of claim 1, wherein the arcuate polymer strips span across substantially all of the inner lingual area and substantially all of the outer labial area of the patient's teeth.

9. The retainer of claim 1, wherein the polymer strips are contoured to match the contour of the corresponding lateral surfaces of the teeth, including the undercuts of the teeth adjacent the gum line.

10. The retainer of claim 9, wherein the polymer strips include formed projections received within the spaces between the lateral surfaces of adjacent teeth.

11. The retainer of claim 1 wherein the first transverse adjusting segment comprises a loop which is selectively compressible to reconfigure the retainer.

12. An orthodontic retainer for fitting a patient's teeth having lingual, labial and buccal surfaces, comprising:

(a) a wire loop formed to wrap around the lingual surfaces and the labial and buccal surfaces of the patient's teeth;

(b) a first polymer strip in which a segment of the wire loop which wraps the lingual surfaces of the teeth is embedded, the first polymer strip being contoured to fill undercuts defined by the lingual surfaces of the teeth;

(c) a second polymer strip in which a segment of the wire loop which wraps the labial and buccal surfaces of the teeth is embedded, the second polymer strip being contoured to fill undercuts defined by the buccal surfaces of the teeth;

(d) wherein the wire loop defines bent adjustment segments free of the first arid second polymer strips, the retainer leaving the patient's palette exposed, the wire loop and polymer strips having sufficient rigidity to maintain the first polymer strip and second polymer strip in a desired spaced-apart disposition contacting the patient's lingual, labial and buccal teeth surfaces while permitting unobstructed occlusion of the teeth.

13. An orthodontic retainer for a patient having right and left sides and teeth which include lingual and labial surfaces, the lingual surfaces of the teeth defining an inner lingual arch-shape extending from one side of the patient to the other, and the labial surfaces of the teeth defining an outer labial arch-shape extending from one side of the patient to the other, the orthodontic retainer comprising:

(a) a wire formed into a loop, the loop including:

(i) a lingual section substantially corresponding in shape to the inner lingual arch-shape defined by the lingual surfaces of the teeth of the patient;

(ii) a labial section substantially corresponding in shape to the outer labial arch-shape defined by the labial surfaces of the teeth of the patient; and (iii) a first transverse adjusting segment for adjusting the length of the loop along at least one of the sections of the loop, the adjusting segment extending arcuately from a section of the loop; and (b) a strip of polymer material in which the lingual and labial sections of the loop are embedded.

14. The orthodontic retainer of claim 13, further comprising a second transverse adjusting segment, wherein one transverse adjusting segment extends from one of the sections of the loop, and the other transverse adjusting segment extends from the other section of the loop.

15. The orthodontic retainer of claim 13, further comprising a distal adjusting segment having a first end and a second end, the first end extending from one of the sections of the loop, and the second end extending from the other section of the loop, wherein the distal adjusting segment forms an arch-shape lying in a plane generally parallel to a plane that one of the sections of the loop lies in.

16. The orthodontic retainer of claim 13, further comprising an artificial tooth connected to the strip of polymer material.

17. The orthodontic retainer of claim 16, wherein the artificial tooth is split to form a lingual half and a labial half.

18. The orthodontic retainer of claim 13, further comprising a second transverse adjusting segment, wherein the sections of the loop each include a right half and a left half, the first transverse adjusting segment extending from the right half of a selected section, and the second transverse adjusting segment extending from the left half the selected section.

19. The orthodontic retainer of claim 13, wherein the teeth include occlusal surfaces, the appliance fitting around the teeth so as to permit unobstructed occlusion of the occlusal surfaces of the teeth.

20. A method for retaining the teeth of a patient in a desired arrangement, the patient having right and left sides and an upper set and a lower set of teeth, the teeth of each set including lingual and labial surfaces, the lingual surfaces of each set of teeth defining an inner lingual arch-shape extending from one side of the patient to the other, and the labial surfaces of each set of teeth defining an outer labial arch-shape extending from one side of the patient to the other, comprising the steps of:

(a) forming a wire into a loop having:
  (i) a lingual section substantially corresponding in shape to the inner lingual arch-shape defined by the lingual surfaces of a selected set of teeth of the patient;
  (ii) a labial section substantially corresponding in shape to the outer labial arch-shape defined by the labial surfaces of the selected set of teeth of the patient; and
  (iii) a first transverse adjusting segment for adjusting the length of the loop along at least one of the sections of the loop, the adjusting segment extending transversely in an arch-shape from a section of the loop;
(b) embedding the lingual and labial sections of the loop in strips of polymer material; and
(c) surrounding the lingual and labial surfaces of the selected set of teeth with the first orthodontic appliance.

21. The method of claim 20, further comprising the step of forming a distal adjusting segment in the loop, the distal adjusting segment having a first end and a second end, the first end extending from one of the sections of the loop, and the second end extending from the other section of the loop, wherein the distal adjusting segment forms a rearwardly extending arch-shape.

22. The method of claim 20, wherein a tooth is missing from the selected set of teeth, further comprising the step of connecting an artificial tooth to the orthodontic appliance for cosmetically replacing the missing tooth.

* * * * *